United States Patent [19]

Nowacki et al.

[11] Patent Number: 4,966,132

[45] Date of Patent: Oct. 30, 1990

[54] REMOTE SPARK SHOCK WAVE GENERATOR

[75] Inventors: Christopher Nowacki, Long Grove; Alfred G. Brisson, Kildeer, both of Ill.

[73] Assignee: Northgate Research, Inc., Arlington Heights, Ill.

[21] Appl. No.: 278,368

[22] Filed: Dec. 1, 1988

[51] Int. Cl.$^5$ .............................................. A61B 17/22

[52] U.S. Cl. .................................. 128/24 A; 606/128

[58] Field of Search ................ 128/24 A, 328, 660.03; 181/106, 118, 120; 367/147; 606/127, 128

[56] References Cited

U.S. PATENT DOCUMENTS 2,559,227 5/1947 Rieber ................................ 128/24 A
4,630,607 12/1986 Duinker et al. ..................... 128/328

*Primary Examiner*—Francis Jaworski
*Assistant Examiner*—K. M. Pfaffle
*Attorney, Agent, or Firm*—Robert M. Wolters

[57] ABSTRACT

Apparatus is provided for the extracorporeal destruction of kidney stones, and includes an ellipsoidal reflector. The reflector has a first focus point, and a second focus point, the reflector being truncated and the second focus point being disposed beyond the resulting open end of the reflector for coincidence with a kidney stone or the like. An extension from the apex of the reflector has a cavity with a spark gap therein. The cavity opens into the reflector, and the cavity and reflector are filled with liquid such as water. A spark produced across the spark gap produces a shock wave which moves to the first focus point of the reflector and is reflected to the second focus point.

9 Claims, 1 Drawing Sheet

REMOTE SPARK SHOCK WAVE GENERATOR

BACKGROUND OF THE INVENTION

Extracorporeal kidney stone disintegrators, known as lithotripters, are well known in the art. A truncated ellipsoidal reflector is filled with water, and is coupled to the body of a patient suffering from kidney stones. A spark gap mechanism is located at one focus point of the ellipsoid within the truncated reflector, and the reflector is positioned adjacent the patient's body so that the second focus point of the ellipsoid lies on the kidney stone to be disintegrated. The reflector is filled with water and the open end of the truncated ellipsoid is closed with a diaphragm which is pressed against the patient's body. A spark is generated across the gap at the focus point of the truncated ellipsoid, and this causes some of the water in the immediate vicinity to be flashed into steam, and a shock wave is generated. The energy of the shock wave is focused on the second focus point of the ellipsoid, and since this lies on the kidney stone, the kidney stone is subjected to rather considerable shock energy, and is fragmented. In a period of time usually on the order of an hour the kidney stone, subjected to repeated shock waves, is fragmented into small particles that pass out with the urine, thereby obviating the necessity of surgery.

The reflector is conventionally made of metal, brass being one satisfactory example. Gas bubbles form in the water in the reflector as a result of steam generation by the spark jumping the gap, by some dissociation of the hydrogen and oxygen constituting the water, and by release of air dissolved in the water. The open end of the reflector is oriented upwardly, and the gas released tends to accumulate beneath the diaphragm where it interferes with energy transfer.

One effective structure for degasification of water in lithotripter is disclosed and claimed in our prior U.S. Pat. No. 4,715,375. This includes a very thin, flexible resilient sack, bag or pouch somewhat in the nature of an upright balloon which encloses the spark gap structure. Gas is retained within this balloon and is readily removed therefrom as discussed in the aforesaid U.S. patent.

We have discovered that occasionally a spark instead of jumping the spark gap structure will jump from the spark gap structure to the metallic reflector. This results in puncturing the balloon, and this in turn requires interrupting the kidney stone disintegration to replace the balloon.

OBJECTS AND SUMMARY OF THE PRESENT INVENTION

It is an object of the present invention to provide a remote spark gap generator in a lithotripter which is disposed externally of the reflector, and therefore cannot produce a spark jumping to the metallic body of the reflector.

More particularly, it is an object of the present invention to provide an insulating chamber communicating with the truncated reflector of a lithotripter and wherein the spark is generated, thereby avoiding any possibility of a spark jumping to the metallic body of the reflector.

In accordance with the principles of the present invention the foregoing and other objects and advantages are attained by the use of a structure similar to that in our prior U.S. Pat. No. 4,715,375, but wherein the lower apex of the reflector is provided with an axial extension of suitable resinous plastic or other insulating material. A chamber is provided within this extension, and has a passageway leading axially of the reflector substantially to the first focus point of the ellipsoidal reflector. The spark gap apparatus is disposed within the insulating extension, and the spark is generated within this insulating extension, with the energy generated thereby being transferred to the ellipsoidal reflector in the vicinity of the first focus point, whereby the energy then continues as reflected by the ellipsoidal reflector to the kidney stone to be disintegrated.

THE DRAWING

The present invention will best be understood from the following specification when taken in connection with the accompanying drawing wherein:

FIG. 1, the sole figure of the drawing, is a longitudinal sectional view of the structure incorporating the present invention.

FIG. 2 is a fragmentary view similar to a portion of FIG. 1, showing a modification of the invention.

DETAILED DESCRIPTION OF THE ILLUSTRATED EMBODIMENT

Figure 1:
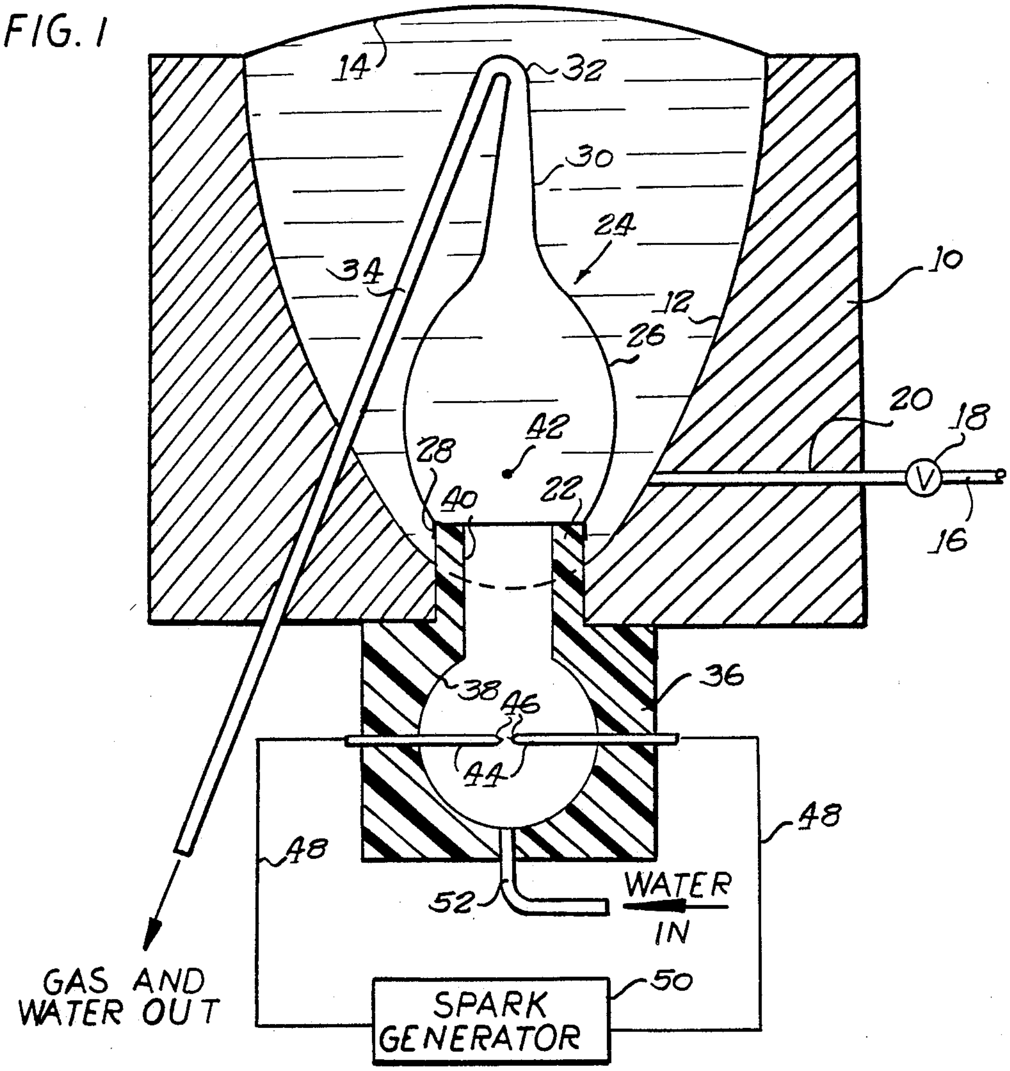

The first portion of the structure as shown herein is substantially the same as shown in our prior U.S. Pat. No. 4,715,375, and includes a metal base or block 10 having a hollow interior in the form of an ellipsoidal reflector 12. A flexible diaphragm 14 is secured across the open top of the reflector at 12 by any suitable means (not shown).

The diaphragm 14 is waterproof as well as flexible, and preferably is made of a suitable elastomeric or plastic resin material. An external water supply pipe 16 is connected to a valve 18 and to a bore or channel 20 in the base to introduce water into the reflector 12, or to drain it, as the case may be.

An upstanding pedestal 22 of epoxy or other suitable plastic resin material extends upwardly through the bottom of the block into the reflector.

A very thin, flexible resilient sack, bag, or pouch 24 is secured to the top of the pedestal by suitable means, and is rather in the nature of an upright balloon. It includes a bulbous ovoid, or egg-shaped lower portion 26 which has an open lower end 28 secured by suitable means such as a retaining band over the upper end of the pedestal. The upper end of the bulbous section 26 opens into an elongated and upwardly directed funnel-like structure 30 tapering to an apex at 32. A length of tubing 34 is secured to the apex by suitable means such as an adhesive, and extends down along the outside of the bag or balloon 24 and out through a bore in the base 10 for evacuation of gas and water.

At its lower end the pedestal 22 is integral with a larger block 36 of epoxy or other suitable plastic resin. The pedestal 22 and the block 36 preferably are cylindrical in exterior configuration for conservative use of material. The block could be square or rectangular in horizontal section, or the block could be spherical in nature. The important thing is that the block is provided with an interior chamber 38 that is shown in the drawing as being spherical. It is believed that spherical is a good shape for directing energy where it is desired, and avoiding cancellation of waves that might occur in other shapes of the chamber. The pedestal is provided with a cylindrical bore 40 leading from the chamber up to the vicinity of the first focus point 42 of the ellipsoidal reflector 12. Electrodes 44 extend through the block 36 in diametral alignment, having tapered inner ends spaced apart at 46 to form a spark gap. The outer ends of the electrode rods 44 are connected by wires 48 to a spark generator 50 including necessary apparatus to provide pulses of high voltage electrical energy to the electrodes to cause a spark to jump the gap 46 on a repeating basis. The bottom of the block is provided with an axial tube or pipe 52 for pumping of water into the chamber 38 and up into the balloon 24, the water then exiting through the tube 34 to insure evacuation of gas bubbles formed as an incident to generation of the shock wave brought about by a spark jumping the gap 46.

When a spark jumps a gap 46 a shock wave is generated. This wave has nowhere to go except straight up to the focus point 42, which is located on the axis of the bore 40, whereupon the shock wave can spread out to the walls of the reflector 12, thereby being focused on the kidney stone (not shown) at the second focus point of the reflector.

Figure 2:
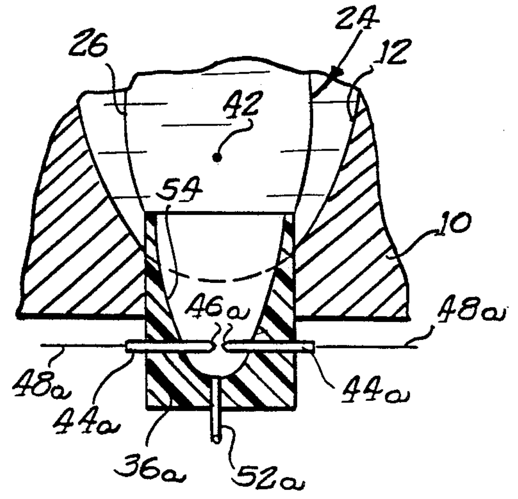

A modification of the invention is shown in FIG. 2. Most of the parts are the same as in FIG. 1, and such parts are identified by identical numerals. Certain parts are similar, but modified, and such parts are identified with similar numerals with the addition of the suffix a. In the embodiment of FIG. 2 the plastic body 36 and upstanding cylindrical projection 22 are replaced by a single cylindrical body **36*a*. The body 36*a* is provided with an internal cavity 54 comprising a truncated portion of an ellipsoidal reflector. Electrodes 44*a* have their tips 46*a* positioned to span the first focus point of the reflecting surface 54, and the reflector 54 is positioned so that the second focus point thereof coincides with the focus point 42 of the principle reflector 12. All of the energy generated by a spark across the gap between the electrode tips 46*a* therefore is concentrated at the focus point 42 of the first or main reflector, whereby it is readily and efficiently reflected to the kidney stone lying on the second focus point of the reflector 12. As will be apparent the longitudinal axis of the ellipsoidal reflecting surfaces 54 and 12 are coincident. Water passes into the ellipsoidal reflectors 54 through tubing 52*a*, and into the balloon 24 as described in connection with FIG. 1, exit being by the same structure as previously described. In FIG. 1 it will be apparent that the axis of the tubular or cylindrical passageway 40 is coincident with the axis of the reflector 12, with the center of the sphere 38** also lying on this axis.

Coincidence of the axes and in the FIG. 1 the center of the sphere as set forth above is believed to be important for maximum transfer of energy to the first focus point 42 of the reflector 12, and for proper disbursement and reflection to the second focus point of the reflector 12.

Various changes in structure will no doubt occur to those skilled in the art, and will be understood as forming a part of the present invention insofar as they fall within the spirit and scope of the appended claims.

The invention is claimed as follows:

1. Apparatus for generating a shock wave comprising an upwardly opening truncated ellipsoidal reflector having its vertex at the lowest portion and opposite the open end, said reflector having first and second focus points, said first focus point being within said reflector relatively adjacent said vertex, said second focus point being disposed beyond said open end, said reflector being adapted to be pressed against a living body with said second focus point coincident with a concretion such as a kidney stone in said living body, an insulating enclosure disposed adjacent said reflector and having a cavity therein adjacent said vertex and opening into said reflector facing said first focus point, means providing a spark gap within said cavity, said reflector and said cavity having a liquid such as water therein, and means for generating a spark across said spark gap, such spark producing a shock wave in said cavity which passes from said cavity to said first focus point and is focused by said reflector on the concretion at the focus point.

2. Apparatus as set forth in claim 1 wherein said reflector has an axis of rotation, and wherein said spark gap lies on said axis.

3. Apparatus as set forth in claim 2 wherein said spark gap is disposed below said apex of said reflector.

4. Apparatus as set forth in claim 1 wherein said cavity comprises a second truncated ellipsoidal reflector with first and second focus points, said spark gap being at the first focus point of said second reflector, and the second focus point of said second reflector being coincident with the first focus point of said first mentioned reflector.

5. Apparatus as set forth in claim 4 wherein the second reflector is smaller than the first mentioned reflector and opens into said first mention reflector through the apex thereof.

6. Apparatus as set forth in claim 4 wherein the first mentioned reflector has a first axis of rotation, and wherein the second reflector has a second axis of rotation, said first and second axes being aligned with one another.

7. Apparatus as set forth in claim 1 wherein said cavity is rotationally symmetric and has an axis of rotation, said reflector having an axis of rotation, the cavity axis and the reflector axis being aligned with one another.

8. Apparatus as set forth in claim 7 wherein said cavity comprises a sphere.

9. Apparatus as set forth in claim 8 wherein the spark gap is coincident with the center of the sphere.

* * * * *